United States Patent [19]
Fox et al.

[11] Patent Number: 5,405,366
[45] Date of Patent: Apr. 11, 1995

[54] ADHESIVE HYDROGELS HAVING EXTENDED USE LIVES AND PROCESS FOR THE PREPARATION OF SAME

[75] Inventors: Adrian S. Fox, New Windsor; Christine A. Czap, Montgomery; Robin R. Wiser, Chester, all of N.Y.

[73] Assignee: Nepera, Inc., Harriman, N.Y.

[21] Appl. No.: 974,449

[22] Filed: Nov. 12, 1992

Related U.S. Application Data

[63] Continuation-in-part of Ser. No. 790,968, Nov. 12, 1991, abandoned.

[51] Int. Cl.$^6$ .................. A61F 13/02; A61L 15/22; A61B 17/00
[52] U.S. Cl. ..................... 607/50; 607/152; 607/153; 604/307; 522/173; 522/181; 427/207.1; 424/78.02; 424/78.05; 424/443
[58] Field of Search ................. 424/78.05, 78.02, 443; 522/173, 181; 427/207.1; 604/307; 602/54; 128/723, 640; 607/152, 153, 50

[56] References Cited

U.S. PATENT DOCUMENTS

| | | |
|---|---|---|
| 3,412,054 | 11/1968 | Milligan et al. |
| 4,094,838 | 6/1978 | Schneider et al. |
| 4,542,176 | 9/1985 | Graham |
| 4,563,184 | 1/1986 | Korol |
| 4,706,680 | 11/1987 | Keusch et al. ............ 128/640 |
| 4,742,112 | 5/1988 | Brauer et al. |
| 4,746,514 | 5/1988 | Warne |
| 4,769,013 | 9/1988 | Lorenz et al. |
| 4,777,954 | 10/1988 | Keusch et al. ............ 128/640 |
| 4,791,175 | 12/1988 | Janssen |
| 4,833,196 | 5/1989 | Janssen |
| 4,860,754 | 8/1989 | Sharik et al. |
| 4,871,490 | 10/1989 | Rosiak et al. |
| 4,889,530 | 12/1989 | Smith et al. |
| 4,904,247 | 2/1990 | Therriault et al. |
| 4,983,181 | 1/1991 | Civerchia ............ 623/5 |
| 4,987,182 | 1/1991 | Creasy |
| 4,989,607 | 2/1991 | Keusch et al. ............ 128/640 |
| 5,002,792 | 3/1991 | Vegoe |
| 5,013,769 | 5/1991 | Murray et al. |
| 5,035,884 | 7/1991 | Song et al. |
| 5,059,189 | 10/1991 | Cilento et al. |
| 5,059,424 | 10/1991 | Cartmell et al. |
| 5,061,689 | 10/1991 | Alvarez |
| 5,077,352 | 12/1991 | Elton |
| 5,106,629 | 4/1992 | Cartmell et al. |
| 5,115,801 | 5/1992 | Cartmell et al. |
| 5,147,071 | 9/1992 | Keusch et al. ............ 128/640 |
| 5,156,601 | 10/1992 | Lorenz et al. |
| 5,179,174 | 1/1993 | Elton |
| 5,219,325 | 6/1993 | Hennink et al. |

FOREIGN PATENT DOCUMENTS

| | | |
|---|---|---|
| 0279118 | 4/1986 | European Pat. Off. |
| 0424165A1 | of 1989 | European Pat. Off. |
| 0455324A1 | 6/1991 | European Pat. Off. |
| 0450671A1 | 9/1991 | European Pat. Off. |
| 89/09246 | 5/1989 | WIPO |
| 91/15250 | of 1991 | WIPO |

OTHER PUBLICATIONS

CasChem, Inc.-Technical Bulletin 100, Baker Press, "Castor Oil"-1982.

*Primary Examiner*—Thurman K. Page
*Assistant Examiner*—Peter F. Kulkosky
*Attorney, Agent, or Firm*—Pennie & Edmonds

[57] ABSTRACT

This invention relates to a non-stringy adhesive hydrophilic gel comprising an aqueous mixture of a radiation crosslinkable water-soluble polymer, at least one humectant effective to extend the moisture retaining characteristics of the gel and which inhibits the ability of radiant energy to crosslink the water-soluble polymer, a pharmacologically active agent, and a crosslinking promoter effective to counteract the crosslinking inhibitory effect of humectant. The aqueous mixture is exposed to radiant energy effective to provide a non-stringy adhesive cohesive homogeneous hydrophilic gel that has an extended in-use lifetime. The gels can be formed into PATCHES for long term application of the pharmacologically active agent to a patient.

66 Claims, 2 Drawing Sheets

ADHESIVE HYDROGELS HAVING EXTENDED USE LIVES AND PROCESS FOR THE PREPARATION OF SAME

This application is a continuation-in-part of applicant's application Ser. No. 07/790,968, filed Nov. 12, 1991, now abandoned, the complete disclosure of which is incorporated by reference herein.

FIELD OF THE INVENTION

The invention is directed to non-stringy adhesive hydrophilic gels (hydrogels) that resist premature loss of water and are capable of extending the useful life of items such as wound dressings, electrodes, cosmetics, ultrasound coupling sheets, topical or transdermal drug delivery systems, or other bodily contact hydrogel-based materials. The radiation crosslinked hydrogels of the invention contain an effective amount of at least one humectant to enable the hydrogels to remain pliable and tacky to the touch for much longer periods than previously known hydrogels.

The properties exhibited by the new hydrogels of the invention allow the use of the hydrogels in a wide variety of applications, some of which have not been previously practicable. In particular, the hydrogels of the invention can be cooled, e.g., at 0° F. for 16 hours, and used as cold packs without substantial loss of flexibility. The hydrogels also can be prepared to exhibit highly conductive properties. Hence, the present hydrogels can be employed in medical electrodes to provide an adhesive electrical contact with a patient's skin. The hydrogels also can be formulated to include pharmacologically active agents and can be employed as "PATCHES" to administer those agents to a patient by absorption of the agent from the gel into the patient's skin.

BACKGROUND OF THE INVENTION

Hydrophilic gels that contain up to 95 percent water are known. Some of these hydrogels were prepared by irradiation crosslinking and exhibited smooth non-tacky surfaces. More recently, hydrogels having interesting surface characteristics, such as adhesiveness, tackiness or non-stringiness, have been described. These hydrophilic gels can be manufactured into sheets and a number of applications have been disclosed which utilize these materials. For example, hydrogel-based wound dressings are available which permit water soluble drugs to migrate though the hydrogel film without disruption of the film's bacterial barrier properties (See, U.S. Pat. No. 3,419,006). Conventional hydrogels can impart a cooling sensation when applied to the skin. This property is desirable in applications that include contact with inflamed or sensitive areas of the body. However, conventional hydrogel dressings do not readily adhere to exposed wound tissue.

Hydrogel sheets adapted for use in medical electrode applications are also known. Manufacturers of these sheets include Promcon, a Division of Medtronic, Inc. (Brooklyn Center, Minn.); Valleylab, Inc., a Division of Pfizer, Inc. (Boulder, Colo.) Biostim, Inc. (Princeton, N.J.); Lectec Corp. (Eden Prairie, Minn.); and Conmed (Utica, N.M.).

Numerous patents disclose hydrophilic gels or medical electrodes that employ them. For instance, U.S. Pat. No. 4,989,607 describes highly conductive hydrogels comprised of a cohesive uniform mixture of poly(vinyl pyrrolidone) ("PVP"), a viscosity-enhancing hydrophilic polymer, and an effective amount of an electrolyte. These hydrogel compositions display non-stringy adhesive cohesive characteristics. However, these materials dry out quickly and must be replaced frequently to maintain the tackiness required to keep the electrode in place.

U.S. Pat. No. 4,904,247 describes a pressure-sensitive hydrophillic laminate composite made up of contiguous layers of a tacky, pressure sensitive hydrophillic polymer blend and a non-tacky hydropic polymer blend. This patent describes a composite structure of uncrosslinked polymer mixtures which require plasticizers to achieve adhesion.

Although U.S. Pat. No. 4,904,247 describes uncrosslinked structures, hydrogels have been described in the art as three-dimensional structures containing crosslinked water soluble polymer and both bound and entrapped water. See N. A. Peppas and A. G. Mikos, "Preparation Methods and Structure of Hydrogels," *Hydrogels in Medicine and Pharmacy: Volume I Fundamentals*, N. A. Peppas, Ed., CRC Press, Inc., Boca Raton, Fla., 1986, Pg. 2. Therefore, by accepted art definitions, the composite structure of U.S. Pat. No. 4,904,247 is not a hydrogel. Absorption of fluids into the gel therefore would tend to dissolve the uncrosslinked, water soluble polymers thereby leading to eventual mechanical failure of a device that employs the gel compositions of U.S. Pat. No. 4,904,247.

U.S. Pat. No. 4,860,754 to Sharik describes a material that possesses adhesive, cohesive, elastomeric and conductive properties and which is composed of a plasticizer, a high molecular weight water-soluble polymer, uncrosslinked PVP as the tackifier and an electrolyte dopant. It is known that materials containing about 20% by weight of water are less subject to drying out, but Sharik found that hydrogels of uncrosslinked PVP which contain up to 40% by weight of water retain both their electrical properties, as well as their adhesive and cohesive properties.

Although examples of hydrogels and medical electrode assemblies are known, these prior materials suffer from one or more characteristics that limit or, in some cases, preclude their utility as adhesive wound dressings, drug delivery systems, medical electrodes or the like. In particular, these prior materials either dry out rapidly, become brittle when cooled, or have adhesive surface characteristics that are lost upon the slightest over-exposure to crosslinking radiation. Also, none of the prior disclosures describe the flexible, non-stringy, adhesive, cold use characteristics of the hydrogels of the present invention. Moreover, none embody the unique combination of such desirable surface and low-temperature pliability properties with the extended in-use moisture retention characteristics of the present invention. Indeed, none are, at the same time, amenable to sterilization by high energy radiation.

SUMMARY OF THE INVENTION

The present invention is directed to a non-stringy adhesive hydrophilic gel comprising an aqueous mixture of a radiation crosslinkable water-soluble polymer, and an amount of at least one humectant effective to extend the in-use moisture retaining characteristics of the gel. The humectant also inhibits the ability of radiant energy to crosslink the water-soluble polymer. The gel also includes a crosslinking promoter effective to counteract the inhibitory effect of the humectant.

In accordance with the invention, an aqueous mixture is exposed to radiant energy effective to provide a non-stringy adhesive cohesive homogeneous hydrophilic gel that has an extended in-use lifetime. The hydrogel (i) retains moisture during use for longer periods than the same hydrogel prepared without added humectant, (ii) remains flexible after being stored at about 0° F. for at least about 16 hours, and (iii) provides a rolling ball distance of at least about 10 mm using a 16.5 mm, 21.7 gram (g) stainless steel ball in a tack rolling ball method (TRBM) test.

The invention also is directed to hydrogels which contain the humectants which further comprise a water-soluble electrolyte effective to provide a highly conductive hydrogel and to reduce the transverse electrical resistance of the hydrogel to an impedance at 60 Hz of less than about 1,000 ohms.

The present invention relates to the surprising discovery that addition of as little as one percent by weight of the total hydrogel formulation of a humectant yields an aqueous hydrophilic polymer composition that resists crosslinking (curing) induced by ionizing radiation, even at radiation dosages that would otherwise be sufficient to overcrosslink aqueous hydrophilic polymer compositions containing no humectant. For example, when a small amount of a humectant, such as glycerol, propylene glycol or poly(ethylene glycol) ("PEG"), is added to aqueous formulations of a water-soluble polymer such as (PVP), poly(ethylene oxide) ("PEO") or blends thereof, the resulting formulations resist crosslinking upon exposure to ionizing radiation in the form of an electron beam at dosages of up to 4 Mrads of absorbed radiation. This amount of radiation would have overcrosslinked previously described aqueous mixtures of water-soluble polymers of the prior art and would have resulted in a hydrogel material with "dead" (i.e., non-adhesive) surface properties. Notably, however, this same amount of radiation is sufficient to sterilize the hydrogel formulations of the invention.

It has also been surprisingly discovered that the resistance to crosslinking observed for the humectant-containing formulations of the invention can be overcome by the addition of small quantities of polyfunctional crosslinking promoters such as acrylic or methacrylic monomer derivatives while retaining the softening and moisture retentive benefits of the humectant additives. It has further been discovered that upon addition of a predetermined amount of crosslinking promoter, that the modified aqueous formulations may be cured, if desired, under substantially the same crosslinking operating conditions as are sufficient to cure aqueous formulations prepared without added humectants or softeners.

Surprisingly, the hydrogels of the invention remain cohesive, adhesive, soft and pliable during active use of the hydrogel for much longer periods of time compared with previously known hydrogels prepared without the added humectant. Preferred hydrogels of the present invention also exhibit non-stringy surface characteristics.

The invention is also directed to highly conductive hydrogels which embody the desirable characteristics of cohesiveness, adhesiveness, softness, sufficient tackiness, non-aggressiveness, non-stringiness and extended use life described above. Thus, these highly conductive, cohesive, homogeneous hydrogels are comprised of a crosslinked mixture of water, electrolyte, water-soluble polymer, humectant and crosslinking promoter.

In another aspect, the invention is directed to hydrogel compositions which contain at least one pharmacologically active agent by providing an aqueous mixture of at least one crosslinkable, water-soluble polymer in an amount effective to provide a crosslinkable hydrophilic gel. Thus gels are made by adding at least one humectant in an amount effective to extend the moisture retaining characteristics of the gel and to inhibit the ability of radiant energy to crosslink the polymer, adding a crosslinking promoter in an amount effective to counteract the crosslink inhibiting effect of the humectant, and including in the composition at least one pharmacologically active agent. The mixture is exposed to radiant energy effective to provide an adhesive homogeneous hydrophilic gel suitable for enabling the pharmacologically active agent to be absorbed into the skin of a patient. Alternatively, the pharmacologically active agent (indeed any desirable active agent) may be incorporated into the gel after irradiation. For instance, the gel can be exposed to an aqueous solution of the active agent for a time sufficient for the active atent to diffuse into the gel. Preferably, the gel which is exposed to the aqueous solution of active agent has been partially or fully dehydrated to better absorb the aqueous solution containing the active agent. Partial or full dehydration can be effected by any means known in the art, such as by heating the gel in an oven or subjecting it to a vacuum.

The hydrogel compositions of the invention have adhesive and cohesive properties which enable the gel, when adhered to a patient's skin, to transfer pharmacologically active agents contained in the hydrogel to the patient. The hydrogel compositions comprise an aqueous mixture of at least one crosslinkable water-soluble polymer in an amount effective to provide a crosslinkable hydrophilic gel; at least one humectant in an amount effective to extend the moisture retaining characteristics of the gel and to inhibit the ability of radiant energy to crosslink the polymer; a crosslinking promoter in an amount effective to counteract the crosslink inhibiting effect of the humectant; and at least one pharmacologically active agent.

In yet another aspect of the invention, a method of treating a patient with pharmacologically active agents is provided. The method entails providing a hydrogel containing at least one pharmacolgically active agent, and contacting the hydrogel to the skin of a patient to permit the pharmacologically active agent in the hydrogel to be absorbed into the skin.

The present invention therefore provides increased in-use lifetime of wound dressings, electrodes, cosmetic dressings, ultrasound coupling sheets, topical or transdermal drug delivery systems, protective drapes or other bodily contact hydrogel-based materials or assemblies.

Definition

The term "humectant" is defined herein as any low molecular weight biocompatible material that increases use life, promotes moisture retention and imparts flexibility and softening properties in hydrogels containing said humectant.

DETAILED DESCRIPTION OF THE INVENTION

Figure 1:
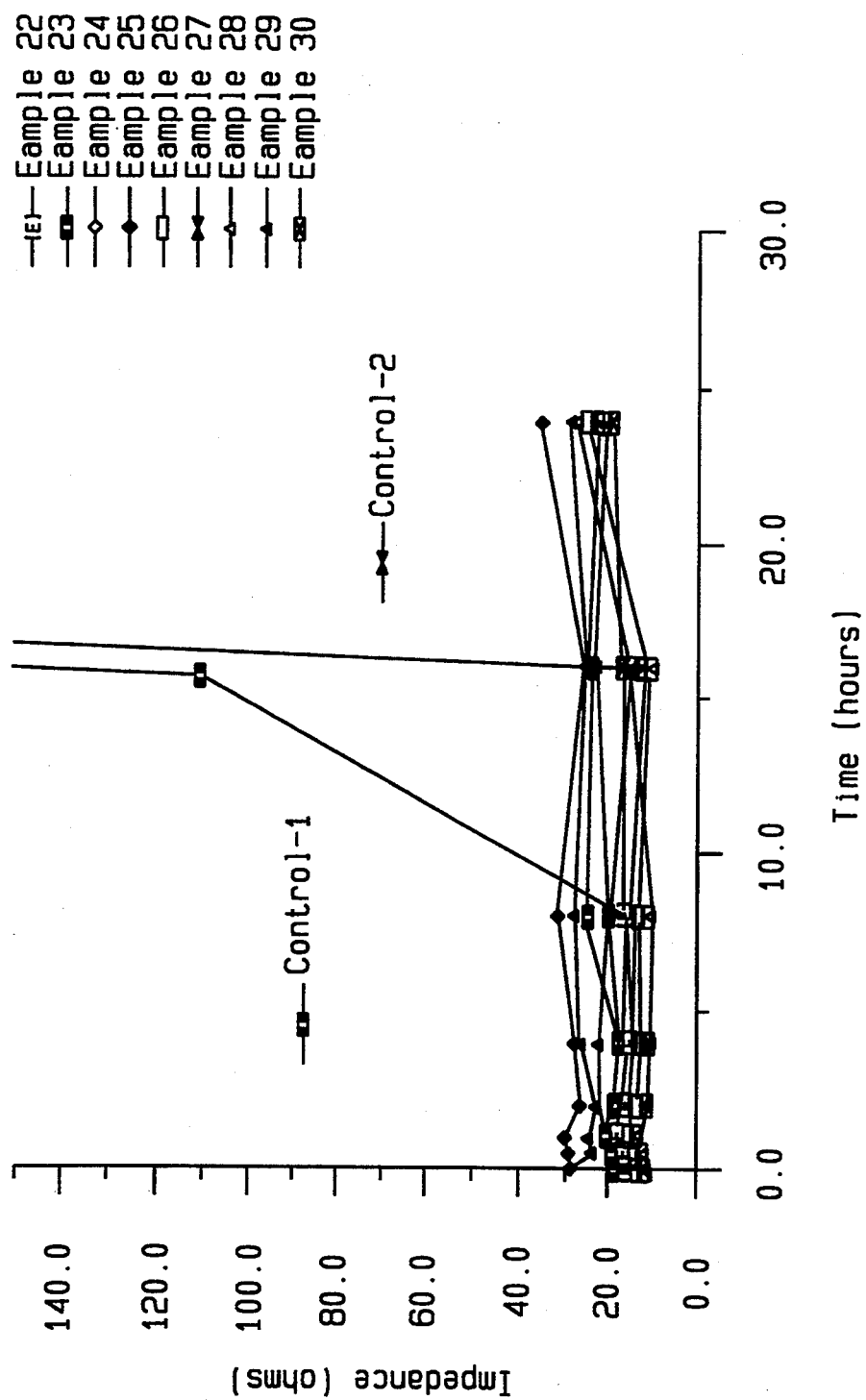
FIG. 1 shows the effects of drying on the impedance of a PEO hydrogel electrode formulation of the present invention.

The hydrogels employed in this invention are unique in that they are substantially free of unbound water. This property is important for several reasons. First, it means that the gel does not "bleed" free water under the influence of pressure or elevated temperatures, which bleeding can adversely affect one or both of the gel's non-stringy adhesiveness or uniformity of conductivity, in the case of conductive formulations. Second, it means that the gel is not "broken" easily if subjected to temperatures near the freezing point of water, but rather the gel is extremely flexible at 0° F. This characteristic is very important for the hydrogel's therapeutic usefulness as a cold pack and from a storage and shipping stability point of view. In addition, the gel's resistance against "bleeding" free water, in turn, contributes to its resistance against drying out after its removal from a sealed gas and moisture impermeable package.

As stated above, the presence of humectant in the hydrogel formulation surprisingly gives rise to a hydrogel that has a longer in-use lifetime than any previously known hydrogel. This latter property is particularly desirable and advantageous because it allows longer uninterrupted medical or therapeutic treatment of an individual with fewer applications and replacement of wound dressings, electrodes, cosmetics, ultrasound coupling sheets, topical or transdermal drug delivery systems such as "PATCHES", protective drapes or other bodily contact hydrogel-based devices.

Because some hydrogel-based products such as medical electrodes, wound dressings, and PATCHES, must be sterile, the packaging of the device should be adaptable to ensure such sterility. Sterilization cannot be achieved conveniently by autoclaving, because heating to extreme temperatures could adversely affect the polymer or alter the moisture content of the gel. Sterility is thus accomplished by other means, e.g., by treatment with ethylene oxide. Since the humectant-containing hydrogels and medical electrode assemblies of the invention are able to withstand higher doses of radiant energy than hydrogels prepared without humectant, the preferred method of sterilization is high energy radiation. Therefore, hydrogel based devices such as medical electrode assemblies and PATCHES may be packaged and subjected to a high energy radiation which converts the starting viscous polymer mixture to a solid hydrogel. Such a process effectively and conveniently sterilizes the hydrogel and associated structural and packaging materials.

The hydrogels employed in this invention are characterized as tacky non-stringy viscoelastic solids which, in the tack rolling ball method (TRBM) test described below, typically give a rolling ball distance of at least about 10 mm. Moreover, these sheets have greater cohesive strength than adhesive strength so that the sheet can be removed from a surface to which it is affixed without leaving a visible residue. Because the sheets of the present gels are integral single structures, much like films of thermoplastic polymers, they have excellent cohesive strength that prevents material from separating from the sheets when they are peeled off the subject's skin.

Unlike the conductive adhesive hydrogels of the prior art, however, the present hydrogels containing humectants are non-stringy and retain moisture longer such that they may be applied and removed repeatedly and remain useful for longer periods of time.

Quite surprisingly then, it has been discovered that cohesive hydrogels containing humectants are sufficiently tacky and adhesive and yet substantially non-stringy for longer periods of time that previous hydrogels. Thus, the application and subsequent removal of the present non-stringy adhesive hydrogels are not accompanied by any discomfort or irritation, both physically and aesthetically.

Not only are these gels substantially or completely free of unbound water, the advantages of which have been discussed above, they are substantially free of discrete polymer particles which could settle out or otherwise adversely affect the physical, electrical or chemical properties of the gels. It should be noted that the hydrogel compositions described herein may exist as a multiphase system comprising high molecular weight macromolecules which are present in the uniform homogeneous mixture. The irradiative crosslinking process "freezes out" these microphase regions to provide a stable highly useful material. In fact, the materials of the present invention remain substantially unchanged, even after a storage period exceeding one year, under ambient conditions and with properly sealed packages. These materials even retain their desirable physicochemical and electrical properties for at least one month at an elevated temperature (e.g., at about 50° C.).

Extrudable Viscous Aqueous Polymeric Mixtures

The hydrogels of the present invention are produced by exposing an aqueous mixture of a water-soluble crosslinkable polymer such as PVP, PEO and combinations thereof, humectants, crosslinking promoters and, optional amounts of pharmacologically active agents or of electroconductive amounts of electrolyte, to high energy ionizing radiation effective to form a solid gel-like material. It has been found that radiation of these extrudable viscous aqueous polymeric mixtures produce cohesive, adhesive, tacky, non-stringy hydrogels with extended in-use lifetimes compared with hydrogels prepared without humectants.

In a particular embodiment of the invention, the water-soluble polymer used is PVP, a polymer of N-vinyl-2-pyrrolidone, having a weight average molecular weight ($M_w$) of about 500 kilodaltons (kD) to about 2,000 kD. In a preferred embodiment of the invention, a PVP polymer having a Mw of about 1,000,000 daltons is employed. Homogeneous aqueous mixtures comprising about 10 to about 30 weight percent of the total formulation (wt %) of PVP and about 1 to about 40 wt % of humectants are suitable for use in the present invention. Preferably, the concentration of PVP in the aqueous mixtures is about 15 to 25 wt %. Radiation crosslinking of PVP mixtures is described in U.S. Pat. No. 4,699,146 and U.S. Pat. No. 4,989,607, the disclosures of which are incorporated herein by reference.

Alternatively, a polymer of ethylene oxide (PEO) can be employed. Preferably, the PEO polymer known as Polyox TM (WRS N-205) available from Union Carbide Corp., having a $M_w$ of 500 to 2,000 kD, most preferably 900 kD, is employed. Homogenous aqueous mixtures comprising 3 to 20 wt % of PEO and 1 to 40 wt % of humectants are suitable to achieve hydrogels for use in the invention. In a preferred embodiment, the concentration of PEO in the aqueous mixture is 7.5 wt. %.

Homogeneous aqueous mixtures comprising about 10 to about 30 wt % of PVP, about 0.1 to about 5 wt % of PEO, about 1 to about 40% humectants and about 0.5 to about 3 wt % of crosslinking promoters are suitable to provide finished hydrogels having the characteristics that achieve the objects of the present invention.

Examples of humectants that can be used in the invention include but are not limited to glycerol, propylene glycol, poly-(ethylene glycol), N-methyl pyrrolidone, N-ethyl pyrrolidone, diacetone alcohol, γ-butyryl lactone, ethyl lactate, low molecular weight polyethylene glycol, or combinations thereof. Preferably, the humectant used in the present invention is biocompatible.

Other humectants which may be employed include mono and di-saccharides such as glucose glutamate, and the like; castor oil and its derivatives, related stearates, oleates, and salts thereof; mixtures of saccharides and sugars; vegetable oil extracts such as monoethanolamine and amide derivatives from esters, triglycerides, as well as fatty acids of vegetable oils. Other oily, high molecular weight, high vapor pressure liquids which are biocompatible and which can be solubilized or dispersed in water also may be used as humectants.

Examples of crosslinking promoters that can be used in the invention include but are not limited to N,N'-methylene-bis-acrylamide, ethylene glycol dimethacrylate or triethylene glycol dimethacrylate.

To reduce the transverse electrical resistance of the homogeneous aqueous mixtures described herein and the hydrogels produced therefrom, a variety of electrolytic substances may be added to the mixtures in amounts sufficient to produce electroconductive products. These electrolytes may be ionizable inorganic salts, organic compounds, or combinations of both. Examples of inorganic salts include, but are not limited to: ammonium sulfate, monoethanolamine acetate, diethanolamine acetate, sodium lactate, sodium citrate, sodium chloride, magnesium sulfate, calcium sulfate, ammonium acetate, magnesium chloride, magnesium acetate, or combinations thereof. Preferably, the electrolyte used is stable and inert upon dissolving in the aqueous mixture and the subsequent radiation crosslinking step. Preferred salts are potassium chloride, sodium chloride, magnesium sulfate, or magnesium acetate. Potassium chloride is most preferred.

Although a wide range of amounts of electrolyte may be present in the mixture, a breakdown in viscosity is observed eventually, as discussed below, and it is preferable to have the water-soluble electrolyte present at a concentration of 0.1 to 10 wt % of the mixture. However, the amount of electrolyte must be effective to reduce the transverse electrical resistance of the mixture, and the resulting hydrogel, to an impedance at 10–60 Hz of less than about 1,000 ohms. Typically, about 5 wt % of an electrolyte such as potassium chloride is sufficient to reduce the impedance at 60 Hz to below about 100 ohms.

Other components also may be present in the non-stringy adhesive hydrogels containing humectants with or without electrolytes of this invention, if so desired. The presence of these additional components may necessitate an adjustment in the dosage of radiant energy applied to the resultant extrudable viscous mixtures to arrive at the non-stringy humectant-containing hydrogels of choice. This adjustment generally requires longer exposure of the multicomponent mixtures to high energy radiation. For instance, additives may be uniformly dispersed in the instant aqueous mixtures (and, consequently, the resulting hydrogels), which additives comprise preservatives, stabilizers, fire retardants, pigments, refractive particles, antifungal agents, bactericides (e.g., silver sulfadiazine), antibiotics, cosmetics (e.g., glycerine, urea, allantoin, sulfur, anthraquinone, hydroquinones), moisturizers, pharmaceuticals, anesthetics (e.g., benzocaine), anti-microbials (e.g., mercurochrome, povidone iodine, iodine), healing agents (e.g., collagen), and the like. These additives may be present in individual or total amounts of about 0.001 to about 3 wt % of the final product.

Specific examples of preservatives include, but are not limited to, Dowicil TM -200 available from Dow Chemical Co., methyl paraben, ethyl paraben, propyl paraben, butyl paraben, paraben salts, Cosmicil TM available from ICI Company, Inc., Glydant TM available from Lonza Co., Germall TM available from ISP Chemicals Co., or combinations thereof. Other formulations for use in topical applications may further comprise boric acid, Burrows solution, and the like.

Preparation of Hydrogels Conductive Sheets Containing Humectants

A hydrogel conductive sheet suitable for use in a medical electrode can be produced by mixing PVP and/or PEO, a humectant, a crosslinking promoter, with or without an electrolyte, and water to form an aqueous mixture. The liquid feed mixture is extruded, preferably onto a flat surface to form a liquid film thereon, e.g., a film of PVP or a PVP-coated substrate such as a scrim, or a sheet of a thermoplastic polymer, such as polyethylene.

The resulting liquid film is subjected to high energy radiation sufficient to convert the film into a non-stringy adhesive solid gel. To facilitate production, the liquid film is preferably backed on one or both sides with a thin peelable hydrophobic sheet, e.g., polyethylene or plastic coated release paper, before it is irradiated. Either or both plastic sheets may be peelably removable after formation of the hydrogel sheet, either before packaging or before use. The hydrogel sheet, which after irradation, is a viscoelastic solid, can be cut to desired size and shape for use as the conductive element that contacts the skin in an electrode device. Depending upon the application, different types of backing sheets can be used on one or both sides of the hydrogel sheet, e.g., a non-peelable sheet can be used on one side only or a peelable sheet on one side, and a non-peelable sheet on the other.

The PVP and/or PEO gel formulations useful as, for example, medical electrode include those which incorporate and bind high concentrations of water while maintaining adequate surface tack (adhesiveness), sufficient strength (cohesiveness), and substantial non-stringiness for long periods of time, even at low temperatures. The multicomponent polymer/salt/humectant/-crosslinking promoter/water mixture should be viscous enough to be extrudable and formable into a sheet-like configuration, e.g., a liquid film of about 5.0 mil to 75 mil thickness, before crosslinking. Preferably, the viscosity of the aqueous mixture exceeds about 8,000 cps.

To contribute to the strength of the hydrogel, both in tension and flexure, a low area-weight scrim can be incorporated during fabrication before crosslinking. The scrim, which is in intimate contact with the hydrogel, can be of mesh type geometry, either woven or nonwoven (e.g., non-woven monofilaments heat sealed together at their interstices or a sheet of thermoplastic polymer with holes in a geometric pattern heat-stamped therein), provided the scrim is of substantial open area and low area weight (e.g., from about 1.0 to 12 mil in thickness and an area weight of about 0.002 to 0.2, preferably about 0.003 to 0.1 g/inch$^2$). Preferably, the scrim and the hydrogel material are present in a range of thickness of about 0.25 to about 2.5 mm. The scrim is preferably fabricated from a synthetic hydrophobic polymer, e.g., a polyethylene, polypropylene, polyester, polyamide homopolymer. These materials are preferably non-plasticized water-insoluble polymers so that they cannot leak impurities into the hydrogel.

If a scrim is incorporated into the body of the mixture, the mixture should project beyond both faces of the scrim and all surfaces of the scrim should be wet with the solution. This casting technique is possible with conventional equipment and can be continuous, thereby forming an elongated continuous sheet or film, or discontinuous, i.e., applying individual segments of the mixture of a size and shape corresponding to single electrodes. Any quantity of the extrudable viscous aqueous mixture may be applied to a backing film to form a sheet of hydrogel capable of yielding a plurality of individual interfacing means for individual electrodes, or a large single sheet which can be cut up to form a plurality of interfacing means. The sheets may also be cut into long strips and rolled like a roll of tape. The thickness of the aqueous film mixture that is applied to the backing sheet is generally dictated by the viscosity of the solution and whether or not a scrim is incorporated therein.

After the viscous mixture is applied or cast to the desired thickness, it is subjected to crosslinking high energy irradiation, such as a high energy electron flux produced by an electron accelerator or Van De Graaf generator. Alpha particles, beta particles, gamma rays, X-rays, electron beams, or high energy ultraviolet radiation may be used effectively to initiate or precipitate the crosslinking of polymer chains. When electrons are employed, the beam of electrons should have sufficient energy to penetrate the mixture completely, so that the mixture receives a radiation dose effective to crosslink the entire cross section of the sample. Proper dose/energy/thickness relationships are readily apparent to those skilled in the art of radiation processing. To achieve the desired degree of uniform crosslinking effective to convert the polymer/salt/humectant/crosslinking promoter/water mixture into a viscoelastic non-stringy adhesive gel-like solid, doses typically of about 0.5 Mrads to about 4 Mrads, and usually about 0.5 to about 2 Mrads are required, depending upon the selected polymer and its concentration, humectant and its concentration, crosslinking promoter and its concentration, the selected salt and its concentration and the presence or absence of selected functional, therapeutic agents or other additives. Most preferably, these formulations are irradiated at a dose of about 0.5 to about 4.0 Mrad.

In a specific embodiment of the invention, a conductive non-stringy adhesive hydrogel is produced from an aqueous mixture comprising 20 wt % PVP, 1 wt % PEO, 30 wt % glycerol, 5 wt % potassium chloride, 0.1 wt % Dowicil ™ -200 available from Dow Chemical Co., 0.02 wt % propyl paraben, 0.15 wt % methyl paraben, 0.02 wt % ethyl paraben, 0.007 wt % butyl paraben, and 1.0 wt % N,N'-methylene-bis-acrylamide. The extrudable viscous aqueous mixture may be irradiated under a variety of dosage conditions (See Examples Section, below, for additional details).

In another embodiment of the invention, an aqueous mixture comprising PEO (7.5 wt %), glycerol (10 wt %,), KCl (5 wt %), 1 wt % N,N'-methylene-bisacrylamide, and Nipasept ™ Sodium 0.26 wt % [(<70 wt %) methyl paraben sodium salt, (>15 wt %) ethyl paraben sodium salt, (>10 wt %) propyl paraben], available from Nipa Laboratories, is irradiated under several dosage conditions, as described further below in the Examples Section, to provide useful hydrogels according to the present invention.

Figure 2:
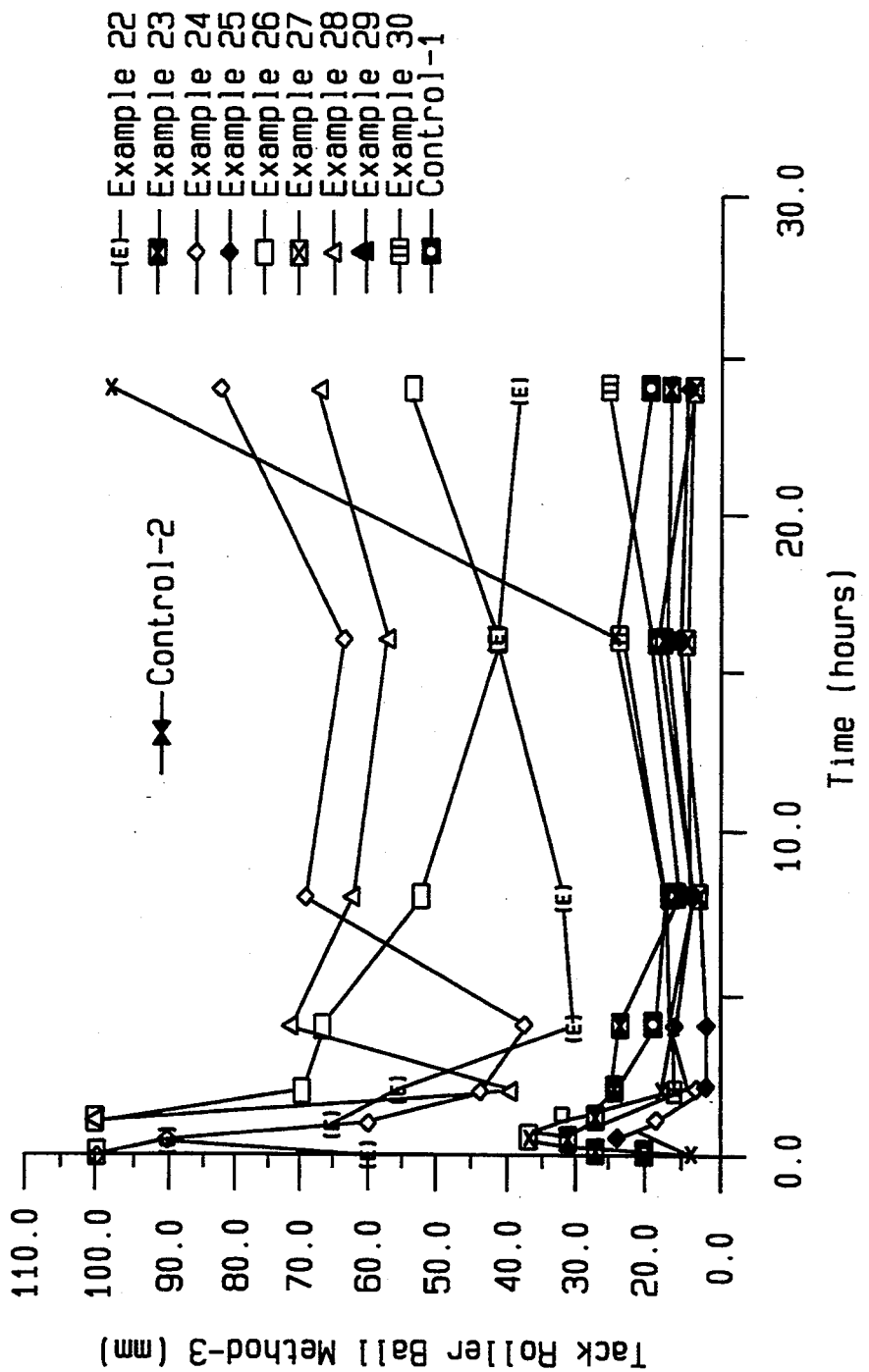
FIG. 2 shows the effects of drying on the adhesive properties, as measured by the TRBM test, for a PEO hydrogel electrode formulation of the present invention.

The physical properties of the resulting hydrogels are disclosed in Tables VI and XII and in FIGS. 1 and 2. The corresponding electrical data on the hydrogels are presented in Table XIV. Most preferably, the hydrogels of the invention have TRBM values of at least about 10 mm.

After the hydrogel sheet is irradiated and converted into a viscoelastic solid, it can be formed into shaped articles such as electrodes or "PATCHES" suitable for adhering to a patient's skin. First it is cut to size, if it is not formed in its desired final shape. If both faces of the hydrogel are covered with backing material, one of its faces is freed from the backing material. In the case of an electrode, the side freed from the backing material is affixed to a non-porous support conductive member, e.g., a material which contains a conductive metal button, snap, or tab of conductive foil-polymer laminate which is capable of receiving an electrode lead wire and connector to an external electrical apparatus. The shaped hydrogel products then can be packaged. The final package preferably is a gas, moisture and microorganism impermeable sealed pouch or envelope, e.g., formed by heat sealing a heat sealable aluminum foil polymer laminate.

When the packaged electrode or PATCH is ready for use, it is removed from its package, the remaining backing material is released by peeling it from the gel interfacing sheet, and it is applied to the skin of the patient. In the case of an electrode, the electrode lead wire is attached to the electrode at the fastener conductive member. Alternatively, the lead wire can be attached to the electrode before the remaining backing material is removed, the backing material then removed and the electrode with the connecting wire attached applied to the skin. Alternatively, the packaged electrode can be provided with its own electrode lead wire already attached. The same sequence of backing material removal and application of the electrode to the skin would then apply without the necessity of attaching a lead wire to the electrode before or during application.

The hydrogel interfacing member of the electrodes and patches of this invention have high adhesive strengths, which means that they can readily be affixed to the skin and will adhere thereto with little risk of accidental detachment by loss of adhesion. At the same time, the hydrogel interfacing member is substantially non-stringy and is, therefore, more comfortable and more readily acceptable to the user. Because the interfacing member is water based, it is relatively immune to the effects of moisture on the skin and will not slide off as a result of perspiration forming while affixed to the skin. They also have high cohesive strengths, which means that they can be removed from the skin after use without leaving any visible residue. Interestingly, although the gels have a high adhesive strength, it is not high enough to pull hairs from the skin or irritate the skin when the gel is removed therefrom. Furthermore, the use of the present gels is not associated with any objectionable sensation. Finally, the hydrogel interfacing member of the electrodes and PATCHES of this invention retain all of these properties for surprisingly longer periods of time and at lower temperatures.

The medical electrodes and PATCHES of this invention contain a sheet of the hydrogel as a skin interfacing member and can assume a wide variety of shapes and construction which are within the skill of the practitioner in the art.

Because the hydrogels lose water under ambient conditions, they are preferably stored in a water and gas impermeable container, e.g., a polyfoil packet formed from the laminated plastic such as that used to store measured amounts of freeze-dried or ground coffee. Sealed envelopes are conventionally produced by heat sealing a pair of sheets of thin plastic around the hydrogel sheet-backing laminate, PATCH, or medical electrode in which a hydrogel sheet is mounted, or by heat sealing the open end of an otherwise sealed packet or envelope formed from a single sheet of the laminate.

If the film or sheet of the hydrogel of the invention is stored separate from the components of the medical electrode or PATCH with which it is to be used, both faces of the hydrogel are preferably covered with a sheet of peelable release liner, e.g., polyethylene. If the sheet of hydrogel is to be stored mounted in the medical electrode with which it is to be used, its exposed face, i.e., the face to be applied to the skin, is covered with a release liner. If both faces are covered with a release liner, optionally different liners can be employed, one of which is more readily removable therefrom than the other, e.g., a sheet of polyethylene covering one face and a sheet of MYLAR plastic covering the other, thereby ensuring that a predetermined face of the film or sheet is exposed first. In some end use applications, one of the faces of the film or sheet is covered with a conductive member in the final electrode assembly. Other variations should be evident to the skilled practitioner.

The present hydrogel sheet or film can be packaged singly or in multiples between the release liner or liners. In Transcutaneous Electrical Nerve Stimulation (TENS) end uses, it is desirable to mount a plurality of spaced apart circles, squares or rectangles of the film or sheet of the hydrogel on a plastic sheet, e.g., a 2 mil film of MYLAR plastic and cover their exposed face with a different release liner, e.g., a 2 mil film of polyethylene or a sheet of polyethylene coated paper release liner. Either or both of the facing films can be appropriately scored to facilitate removal of the units of hydrogel sequentially. If desired, one face of a plurality of units of the hydrogel can be covered with a large backing sheet, one facing film which is unscored and the other face covered with a release liner of the same dimensions as the units of the hydrogel so that a unit of the hydrogel and the latter release liner can be peeled off together, one at a time from the large backing sheet.

In another embodiment, a large sheet of a laminate formed from hydrogel and films of plastic covering its faces, e.g., a film of polyethylene on one face and a film of MYLAR on the other, is scored at spaced intervals in both directions to produce a plurality of severable square or rectangular units of the laminate, each for use individually in conjunction with a medical electrode by tearing the laminate along a pair of perpendicularly positioned lines, thereby releasing a unit of the laminate from the sheet.

When the sheet of conductive hydrogel is of the same dimension as a release liner covering an exposed face thereof, removal of the latter is facilitated if the latter is slit into pieces, thus providing an edge which can be easily raised with a fingernail or tool.

If desired, a plurality of circles, squares or rectangles of the hydrogel with a release liner covering one face can be "stacked" one upon the other so that a column of such units of the hydrogel sheet with both faces covered with a release liner is formed. Desirably, in such an arrangement, one side of the release liner has a higher adhesive value than the other, so that only one unit of the hydrogel is removed at a time from the column. Such columns can be conveniently stored in glass jars or an aluminum lined paper tube within a moisture impervious sealed container.

The electrode assemblies according to this invention are suitable for application to skin in connection with both electrical signal sensing medical electrical apparatus and electrical energy transmitting medical electrical apparatus, i.e., they can be used both as sensing electrodes and as working electrodes. Examples of "sensing" electrodes are those used in electrocardiogram (ECG), electrooculogram (EOG), electrogastrogram (EGG), surface electromyogram (EMG), electrodermal responses (EDR), electroencephalograms (EEG), visual evoked potential (VEP), and auditory evoked responses (AER). Moreover, because the hydrogels employed therein are biologically inert, the assemblies according to this invention are suited to the detection of signals requiring application to or implanted within sensitive areas of the body, such as the cornea in the electroretinograms (ERG), or in body cavities where the materials of conventional assemblies may prove unsatisfactory, such as in the summated electrocochleograms (ECOG) electro-olfactorograms (EOGS) and measuring electrovaginal potentials (EVP).

Examples of "working" electrodes for which the electrode assemblies of this invention can be used are those adapted structurally for TENS, use as a Electro-Surgical Unit (ESU), External Cardiac Pacing (ECP) and for Defibrillation (DEFIB).

Test Methods

As stated above, the hydrogels employed in this invention are characterized by long use life surface adhesiveness, and sufficient cohesiveness to maintain structural integrity when being removed from the skin. Preferred embodiments are also substantially non-stringy.

The manner and the increased length of time in which the hydrogel film of this invention adheres to the skin is an important aspect of this invention. The hydrogel adheres sufficiently to both dry, damp, clean, or soiled skin. It is tolerant to perspiration which forms from the skin under the hydrogel after applied to the skin because the hydrogel can absorb a substantial amount of water before it loses its surface tack. Conversely, because it is 45+% water, it does not create chemical bonds with the skin and hair which results in pain and/or skin damage when an electrode employing a conventional adhesive-based skin interfacing member is removed after use, and, because it is substantially non-stringy, the present hydrogel is much more comfortable in its use and is less objectionable, less sticky to the touch.

To test for skin adhesiveness, samples of the hydrogel with backing removed from one side can be applied to the skin and left on. This step is done with the scrim-containing hydrogel films alone and with a scrim-containing hydrogel film attached to a support backing bearing a metal conductive snap electrical terminal. How well the hydrogel adhered to the skin is observed and how easily the electrode material can be separated from the skin is noted, along with whether or not any residue is left on the skin.

The adhesiveness and tackiness of the conductive hydrogel sheet of films can be quantified by the TRBM test as specified by the Pressure Sensitive Tape Council. This test method for adhesive materials is detailed in The American Society for Testing Materials, Designation D3121-73 (Re-approved 1979) which test method is under jurisdiction of ASTM Committee D-14 on Adhesives. The test utilizes an inclined trough which can be obtained from the Pressure Sensitive Tape Council, 1201 Waakegan Road, Glenview, Ill. 60025. The trough is equipped with a release lever at the top though which a 16.5 mm diameter, 21.7 g steel ball is released onto the trough. The ball gains momentum as it descends the incline and rolls onto the adhesive surface whose adhesiveness is being measured. The shorter the distance the ball travels thereon, the higher the adhesion value.

The TRBM test is performed as follows after the backing material is removed from one side of a hydrogel sample cut one inch wide and at least three inches long. The test is run in a controlled environment (72° F.+/−50° F. and 50%+/−10% relative humidity). A hard, horizontal surface of sufficient size to conduct the test is selected. Both metal and glass plates have proved satisfactory. Before testing each adhesive sheet, clean the inclined trough thoroughly with isopropanol.

The specimen to be tested is placed flat, adhesive side up, in line with the inclined trough. The end of the specimen opposite the incline is held to the table. Only one test is run on each specimen. Each time before the ball is rolled onto the hydrogel, it is thoroughly cleaned with distilled water, isopropanol, or another appropriate solvent which removes any residue that might otherwise remain from a previous test, and then wiped with a lint-free, bleached, absorbent material to remove any remaining residue. After cleaning, the ball or raceway is not touched. Clean, dry tongs are used to place the ball on the upper side of the release. The ball is released and rolls to a stop on the adhesive material. The average of the stopping distance measurements of five or more tests is recorded. Pertinent additional comments based on visual inspection such as noticeable residue on ball, lift of adhesive from substrate, etc., are noted.

In this test, the hydrophilic gels employed in the electrodes of this invention have tack rolling ball distances of at least about 10 mm, and preferably 15 mm or more. The preferred gels have distances of less than about 60 mm. Generally, those hydrophilic gels which provide distances of 25 to 50 mm are advantageous.

EXAMPLES (1–4): Hydrogels Containing Humectants Resist Crosslinking Using Ionizing Radiation From An Electron Beam Up To 3.8 Mrads Of Absorbed Radiation Examples 1–4

Feedmix Preparation: To a solution of 438 g. of steam distilled water (73.0 Wt-%) and 120 g. of humectant (20.0 Wt-%), 42 g. of Polyox ™ WRS N-205 poly-(ethylene oxide) (7.0 Wt-%) from Union Carbide is added slowly with rapid agitation. After the polymer appears to be completely dispersed, agitation is slowed and permitted to continue for 16 hours.

The solutions are analyzed for solids content, (loss on drying) and solution viscosity. See Table I.

TABLE I

| EXAMPLE | HUMECTANT | LOSS ON DRYING (USP-LOD - 105° C. for 1-Hr.) | SOLUTION VISCOSITY (BROOKFIELD "B" SPINDLE @ 10 RPM) |
|---|---|---|---|
| 1 | Polyethylene Glycol-200 | 26.7% | 39,000 cps |
| 2 | Polyethylene Glycol-400 | 27.6% | 25,700 cps |
| 3 | Propylene Glycol | 8.1%* | 35,000 cps |
| 4 | Glycerol | 28.4% | 29,000 cps |

*The propylene glycol appears to have been "flashed off" on drying.

The feedmixes of Examples 1–4 are each coated onto a 3-mil low density polyethylene (LDPE) sheet at 50–60 mils thickness using a doctor blade. The films are covered with a 3-mil LDPE sheet and are cured by irradiating with a 1.5-MeV van der Graaf electron accelerator at 0.95 milliamps beam current and 3.5 meters/minute conveyer line speed to produce an absorbed dose of 3.8 Mrads. The results of the curing are found in Table II.

TABLE II

| EXAMPLE | HUMECTANT | REMARKS |
|---|---|---|
| 1 | Polyethylene Glycol-200 | Feedmix not cured |
| 2 | Polyethylene Glycol-400 | Feedmix not cured |
| 3 | Propylene Glycol | Feedmix not cured |
| 4 | Glycerol | Feedmix not cured |

EXAMPLES (5–30): Hydrogels Containing Humectants And Crosslinking Promoters

Example 5

To 275 g of the feedmix prepared in Example 4 and warmed to 45°–50° C., 1.8 g of N,N'-methylene-bis-acrylamide (0.7 Wt-%) is added slowly, and the feedmix is agitated slowly for 16 hours. The feedmix is coated onto a 3-mil LDPE sheet at 50–60 mils using a doctor blade. The coated film is covered with a 3-mil LDPE sheet and is irradiated with a 1.5 MeV van der Graaf electron accelerator at 0.90 milliamps beam current and 3.5 meters/minute conveyer line speed to produce an absorbed dose of 3.4 Mrads. The feedmix appears to have crosslinked to an adhesive (sticky) hydrogel. Approximately 10 milliliters (ml) of feedmix is similarly cured in a small polyethylene "zip-lock" pouch and is placed in the freezer at approximately 0° F. for 16 hours. The cured hydrogel remains soft to the touch, while a hydrogel prepared without glycerol is stiff to the touch.

Example 6

To 720 g of steam distilled water (72.0 Wt-%) at 45°–50° C., 200 g of glycerol (20.0 Wt-%), 10 g of N,N'-methylene-bis-acrylamide (1.0 Wt-%) and 70 g of Polyox ™ WRS N-205 poly-(ethylene oxide), (PEO) (7.0 Wt-%) are added with rapid agitation. This solution is stirred at room temperature for 16 hours, after which it is poured to a depth of ⅜-inch into a 3.5 inch diameter petri dishes and is cured by a 2.8-MeV Van Der Graaf electron accelerator at 0.9 milliamps beam current and 56 inches/minute conveyer line speed to produce an absorbed dose of 1.35 Mrads. The petri dishes are passed under the beam twice with opposite sides of the gel facing up. The resulting hydrogels are soft to the touch and remain so after being placed in a freezer at approximately 0° F. for 16 hours.

Examples 7–9

Feedmixes based on a poly(vinyl pyrrolidone) and poly(ethylene oxide) as a viscosity enhancer are prepared from the formulations given in Table III.

TABLE III

| RAW MATERIALS | EXAMPLE 7 [G. (WT %)] | EXAMPLE 8 [G. (WT %)] | EXAMPLE 9 [G. (WT %)] |
|---|---|---|---|
| Plasdone TM K-90 (PVP)[1] | 80.0 (20.0) | 60.0 (20.0) | 60.0 (20.0) |
| Polyox TM WRS N-205 (PEO) | 4.0 (1.0) | 3.0 (1.0) | 3.0 (1.0) |
| Distilled Water | 312.64 (78.16) | 144.91 (48.3) | 141.91 (47.3) |
| Glycerol | — | 90.0 (30.0) | 90.0 (30.0) |
| Potassium Chloride | — | — | — |
| Methyl Paraben | 1.0 (0.25) | 0.45 (0.15) | 0.45 (0.15) |
| Ethyl Paraben | 0.12 (0.03) | 0.06 (0.02) | 0.06 (0.02) |
| Propyl Paraben | 0.20 (0.05) | 0.06 (0.02) | 0.06 (0.02) |
| Butyl Paraben | 0.04 (0.01) | 0.02 (0.007) | 0.02 (0.007) |
| Phenoxyethanol | 2.0 (0.5) | 1.5 (0.5) | 1.5 (0.5) |
| N,N'-Methylene-bis-acrylamide | — | — | 3.0 (1.0) |

[1]From International Specialties Corp.

The feedmixes of Examples 7–9 are each coated onto a 3-mil LDPE sheet at 50–60 mils using a doctor blade. The coated films are covered with a polyethylene non-woven scrim (0.016 g/in² in area weight) and 3-mil LDPE sheet and are irradiated with a 1.5-MeV van der Graaf electron accelerator at 0.9 milliamps beam current and 12 meters/minute conveyer line speed to produce an absorbed dose of 1.15 Mrads. The results of the curing are found in Table IV.

TABLE IV

| EXAMPLE | AREA WEIGHT (G/FT²) | TRBM(3)* (mm) |
|---|---|---|
| 7 | 135. | 23 |
| 8 | Does not cure. | Does not cure. |
| 9 | 133. | 30 |

*TRBM(3) is Tack Rolling Ball Method as per PSTC (Pressure Sensitive Tape Council) Test Method #6 using a 16.5 mm in diameter, 21.7 g stainless steel ball.

Thus, formulations containing glycerol will not crosslink appreciably unless crosslinking promoters such as N,N'-methylene-bis-acrylamide are included in the formulation.

Examples 10–12

Electrically conductive feedmixes based on a poly-(vinyl pyrrolidone) and poly-(ethylene oxide) as a viscosity enhancer are prepared as described in Table V.

TABLE V

| RAW MATERIALS | EXAMPLE 10 [G. (WT %)] | EXAMPLE 11 [G. (WT %)] | EXAMPLE 12 [G. (WT %)] |
|---|---|---|---|
| Plasdone TM K-90 (PVP) | 80.0 (20.0) | 60.0 (20.0) | 60.0 (20.0) |
| Polyox TM WRS N-205 (PEO) | 4.0 (1.0) | 3.0 (1.0) | 3.0 (1.0) |
| Distilled Water | 313.64 (73.56) | 144.91 (43.70) | 141.91 (42.7) |
| Glycerol | — | 90.0 (30.0) | 90.0 (30.0) |
| Potassium Chloride | 20.0 (5.0) | 15.0 (5.0) | 15.0 (5.0) |
| Methyl Paraben | 1.0 (0.25) | 0.45 (0.15) | 0.45 (0.15) |
| Ethyl Paraben | 0.12 (0.03) | 0.06 (0.02) | 0.06 (0.02) |
| Propyl Paraben | 0.20 (0.05) | 0.06 (0.02) | 0.06 (0.02) |
| Butyl Paraben | 0.04 (0.01) | 0.02 (0.007) | 0.02 (0.007) |
| Phenoxyethanol | 0.3 (0.1) | 0.3 (0.1) | 0.3 (0.1) |
| N,N'-Methylene-bis-acrylamide | — | — | 3.0 (1.0) |

The feedmixes of examples 10–12, which have solution conductivities of 43,000 μMHOS/cm, 30,000 μMHOS/cm and 34,000 μMHOS/cm, are each coated onto a 3-mil LDPE sheet at 50–60 mils using a doctor blade. The coated films are covered with a polyethylene non-woven scrim (0.016 g/in² in area weight) and 3-mil LDPE sheet and are irradiated with a 1.5-MeV van der Graaf electron accelerator at 0.9 milliamps beam current and 12 meters/minute conveyer line speed to produce an absorbed dose of 1.15 Mrads. The results of the curing are found in Table VI.

TABLE VI

| EXAMPLE | AREA WEIGHT (G/FT²) | TRBM(3)* (mm) |
|---|---|---|
| 10 | 140. | 21 |
| 11 | Does not cure. | Does not cure. |
| 12 | 130. | 28 |

*TRBM(3) is Tack Rolling Ball Method as per PSTC (Pressure Sensitive Tape Council) Test Method #6 using a 16.5 mm in diameter, 21.7 g stainless steel ball.

Examples 13–15

Similar experiments are run on polyethylene oxide formulations using both N,N'-methylene-bisacrylamide and ethylene glycol dimethacrylate. These formulations are listed in Table VII.

TABLE VII

| RAW MATERIALS | EXAMPLE 13 [G. (Wt %)] | EXAMPLE 14 [G. (WT %)] | EXAMPLE 15 [G. (WT %)] |
|---|---|---|---|
| Polyox TM WRS N-205 (PEO) | 75.0 (7.5) | 75.0 (7.5) | 75.0 (7.5) |
| Distilled Water | 687.4 (68.74) | 678.8 (67.88) | 687.4 (68.74) |
| Glycerol | 200.0 (20.0) | 200.0 (20.0) | 200.0 (20.0) |
| Nipasept TM - Sodium | 2.60 (0.26) | 2.60 (0.26) | 2.60 (0.26) |
| Ganex TM P904 | 5.0 (0.50) | 5.0 (0.50) | 5.0 (0.5) |
| Ethylene glycol dimethacrylate | — | 38.6 (3.86) | 30.0 (3.0) |
| N,N'-Methylene-bis-acrylamide | 30.0 (3.0) | — | — |

The feedmixes of examples 13–15 are each coated onto a 3-mil LDPE sheet at 50–60 mils using a doctor blade. The coated films are covered with a polyethylene non-woven scrim (0.016 g/in² in area weight) and 3-mil LDPE sheet and are irradiated with a 1.5-MeV van der Graaf electron accelerator at 0.9 milliamps beam current and 7.7 meters/minute conveyer line speed to produce an absorbed dose of 1.19 Mrads. The results of the curing are found in Table VIII.

TABLE VIII

| EXAMPLE | AREA WEIGHT (G/FT²) | TRBM(3) (mm) |
|---|---|---|
| 13 | 130 | 44 |
| 14 | 130 | 19 |
| 15 | 130 | 12 |

After the hydrogel surface is exposed to the air at room temperature for 16 hours, the surfaces of samples of Examples 10 and 12–15 are examined for surface tack and feel. The surface of Example 10, which did not contain humectant, is hard and stiff. The surfaces of Examples 12–15 are soft and somewhat sticky.

Examples 16–21

Similar experiments are run on polyvinyl pyrrolidone formulations using both glycerol and N,N'-methylene-bis-acrylamide. These formulations are listed in Table IX.

TABLE IX

| RAW MATERIALS | EXAMPLE 16 [G. WT %)] | EXAMPLE 17 [G. WT %)] | EXAMPLE 18 [G. WT %)] | EXAMPLE 19 [G. WT %)] | EXAMPLE 20 [G. WT %)] | EXAMPLE 21 [G. WT %)] |
|---|---|---|---|---|---|---|
| Plasdone TM K-90 (PVP) | 150. (15.0) | 200. (20.0) | 250. (25.0) | 150. (15.0) | 200. (20.0) | 250. (25.0) |
| Distilled Water | 632.4 (63.24) | 582.4 (58.24) | 532.4 (53.24) | 642.4 (64.24) | 582.4 (58.24) | 472.4 (47.24) |
| Propylene glycol | — | — | — | 200.0 (20.0) | 200.0 (20.0) | 250.0 (25.0) |
| Glycerol | 200.0 (20.0) | 200.0 (20.0) | 200.0 (20.0) | — | — | — |
| Nipastat TM * | 2.60 (0.26) | 2.60 (0.26) | 2.60 (0.26) | 2.60 (0.26) | 2.60 (0.26) | 2.60 (0.26) |
| Phenoxyethanol | 5.0 (0.50) | 5.0 (0.50) | 5.0 (0.5) | 5.0 (0.5) | 5.0 (0.5) | 5.0 (0.5) |
| Ethylene Glycol Dimethacrylate | — | — | — | — | 10.0 (1.0) | 20.0 (2.0) |
| N,N'-Methylene-bis-acrylamide | 10.0 (1.0) | 10.0 (1.0) | 10.0 (1.0) | — | — | — |

*Nipa Laboratories, Inc., contains 57% methyl paraben, 14% ethyl paraben, 7% propyl paraben and 22% butyl paraben.

The feedmixes of examples 16–21, which have solution viscosities of 22,000 cps, 63,500 cps, 105,000 cps, 19,500 cps, 35,000 cps and 52,500 cps, respectively, are each coated onto a 3-mil LDPE sheet at 50–60 mils using a doctor blade. The coated films are covered with a polyethylene non-woven scrim (0.016 g/in$^2$ in area weight) and 3-mil LDPE sheet and are irradiated with a 1.5-MeV van der Graaf electron accelerator at 0.9 milliamps beam current and 12 meters/minute conveyer line speed to produce an absorbed dose of 1.15 Mrads. The results of the curing are found in Table X.

TABLE X

| EXAMPLE | AREA WEIGHT (G/FT$^2$) | TRBM(3) (mm) |
|---|---|---|
| 16 | 135 | 20 |
| 17 | 128 | 17 |
| 18 | 133 | 10 |
| 19 | Does not cure. | Does not cure. |
| 20 | 130 | 29 |
| 21 | 138 | 20 |

After the hydrogel surface is exposed to the air at room temperature for 16 hours, the surfaces of samples of Examples 16–18 and 20–21 are examined for surface tack and feel. The surfaces of these samples are soft and somewhat sticky.

Examples 22–30

In these examples, the effects of humectant concentration, crosslinker concentration and crosslinking dose on the drying out of PEO-based hydrogel electrodes were examined. These hydrogel formulations are listed in Table XI.

The feedmixes described in examples 22 to 30 are each coated on a 3-mil LDPE sheet at 50 mil using a doctor blade. The coated films are covered with a polyethylene non-woven scrim (0.016 g/in$^2$ in area weight) and 3-mil LDPE sheet and are irradiated with a 1.5-MeV van der Graaf electron accelerator to produce the absorbed doses described in the design above. The details of this study are given in Table XI and the feedmix properties are listed in Table XII.

TABLE XI

| RAW MATERIALS | EX. 22 [G. (WT %)] | EX. 23 [G. (WT %)] | EX. 24 [G. (WT %)] | EX. 25 [G. (WT %)] | EX. 26 [G. (WT %)] | EX. 27 [G. (WT %)] | EX. 28 [G. (WT %)] | EX. 29 [G. (WT %)] | EX. 30 [G. (WT %)] |
|---|---|---|---|---|---|---|---|---|---|
| Polyox TM WRS 205 | 90.0 (7.5) | 90.0 (7.5) | 90.0 (7.5) | 90.0 (7.5) | 90.0 (7.5) | 90.0 (7.5) | 90.0 (7.5) | 90.0 (7.5) | 90.0 (7.5) |
| D.I. Water | 914.9 (76.24) | 554.9 (46.24) | 902.9 (75.24) | 542.9 (45.24) | 914.9 (76.24) | 554.9 (46.24) | 902.9 (75.24) | 542.9 (45.24) | 728.9 (60.74) |
| Potassium Chloride | 60.0 (5.0) | 60.0 (5.0) | 60.0 (5.0) | 60.0 (5.0) | 60.0 (5.0) | 60.0 (5.0) | 60.0 (5.0) | 60.0 (5.0) | 60.0 (5.0) |
| N,N'-Methylene-bis-acrylamide | 12.0 (1.0) | 12.0 (1.0) | 24.0 (2.0) | 24.0 (2.0) | 12.0 (1.0) | 12.0 (1.0) | 24.0 (2.0) | 24.0 (2.0) | 18.0 (1.5) |
| Nipasept TM Sodium* | 3.1 (0.26) | 3.1 (0.26) | 3.1 (0.26) | 3.1 (0.26) | 3.1 (0.26) | 3.1 (0.26) | 3.1 (0.26) | 3.1 (0.26) | 3.1 (0.26) |
| Glycerol | 120.0 (10.0) | 480.0 (40.0) | 120.0 (10.0) | 480.0 (40.0) | 120.0 (10.0) | 480.0 (40.0) | 120.0 (10.0) | 480.0 (40.0) | 300.0 (25.0) |
| Croslinking Dose (Mrads) | 0.5 | 0.5 | 0.5 | 0.5 | 2.0 | 2.0 | 2.0 | 2.0 | 1.25 |

*Nipa Laboratories, Inc., contains <70% methyl paraben sodium salt, >15% ethyl paraben sodium salt, >10% propyl paraben sodium salt.

TABLE XII

| EXAMPLES | SOLUTION VISCOSITY (CPS) | SOLUTION CONDUCTIVITY ($\mu$MHOS) | %-SOLIDS (LOD-USP) |
|---|---|---|---|
| 22 & 26 | 18,300 | 58,000 | 24.02 |
| 23 & 27 | 41,700 | 15,500 | 53.45 |
| 24 & 28 | 25,900 | 43,500 | 24.52 |
| 25 & 29 | 45,000 | 16,100 | 54.17 |
| 30 | 31,300 | 29,500 | 38.17 |

Examples 22–30 were tested for the effect of drying at ambient conditions (19.1° C. and 88% relative humidity). The results are in Table XIII and FIGS. I and II, in which the impedance (bulk resistivity) and adhesivity (TRBM-1 and -3) of examples 22–30 are compared with "control" electrode formulations from U.S. Pat. No. 4,989,607 and U.S. Pat. No. 4,706,680. These "control" formulations do not contain humectants. While examples 22–30 have acceptable bulk resistivities after 24 hours, both "control" formulations are no longer usable.

Multiple linear regression analysis of data in Table XIII produces the following prediction equations and correlation coefficients ($r^2$-values):

$$\text{IMPEDANCE} = -1.24 + 0.24x\text{-}(\text{GLYCEROL}) + 8.25x(\text{MBA})^* + 1.50x(\text{DOSE})$$
$$R^2 = 0.85$$

TRBM
$$(1) = 15.04 - 1.63x(\text{GLYCEROL}) + 19.25x\text{-}(\text{MBA}) + 15.52x(\text{DOSE}) \; R^2 = 0.57$$

TRBM
$$(3) = 73.51 - 2.54x(\text{GLYCEROL}) + 19.75x\text{-}(\text{MBA}) + 16.50x(\text{DOSE}) \; R^2 = 0.68$$

(*MBA = N,N'-methylene-bis-acrylamide)

The prediction, i.e. regression equation is derived from the coefficients or effects, i.e., the responses that change in the independent variable has on the dependent variable, obtained in a regression analysis. The prediction equation can be used to model the behavior of a process in response to change in the variables controlling that process. G. E. P. Box, W. G. Hunter and J. S. Hunter, *Statistics for Experimenters: An Introduction to Design, Data Analysis, and Model Building*, John Wiley & Sons, Inc., New York, 1978, pages 309–328.

the partial or complete removal of water. A solution or dispersion of the same or different drug may be introduced into the dried hydrogel. The resulting hydrogels can be formed into PATCHES which can be adhesively attached to the skin of a patient for long term transmittal of the active agent to the patient. The amounts of active agents which can be included in the gel can vary from 0–50% of the gel, preferably at least 5%.

Pharmacologically active agents which may be included in the hydrogels include but are not limited to topical analgesics such as benzocaine and phenol, hydrocortisone, camphor, lidocaine, trolamane, salicylate, and the like; narcotics such as morphine and the like; topical-counter irritants such as methyl salicylate and menthol, capsaicane and the like; antiseptics such as chlorhexidine glyconate, and the like; appetite suppressants such as phenylpropanolamine hydrochloride, and the like; asthma relief preparations such as epinephrine hydrochloride, and the like; decongestants such as menthol with camphor and oil of eucalyptus, and the like; preparations including corn, warts and callous remov-

TABLE XIII

| | TIME (HOURS) | | | | | | | | | | | |
|---|---|---|---|---|---|---|---|---|---|---|---|---|
| | 0.0 | | | 0.5 | | | 1.0 | | | 2.0 | | |
| EX. | IMPEDANCE (OHMS) | TRBM (1)* (mm) | TRBM (3) (mm) | IMPEDANCE (OHMS) | TRBM (1) (mm) | TRBM (3) (mm) | IMPEDANCE (OHMS) | TRBM (1) (mm) | TRBM (3) (mm) | IMPEDANCE (OHMS) | TRBM (1) (mm) | TRBM (3) (mm) |
| 22 | 11.0 | 10.1 | 60.0 | 11.0 | 6.0 | 90.0 | 12.5 | 13.0 | 65.0 | 10.5 | 6.0 | 56.0 |
| 23 | 16.5 | 1.0 | 29.0 | 17.5 | 1.0 | 32.0 | 19.0 | 1.0 | 27.0 | 19.0 | 1.0 | 24.0 |
| 24 | 17.0 | 43.0 | 100.0 | 16.5 | 28.0 | 91.0 | 16.5 | 25.0 | 60.0 | 16.0 | 8.0 | 44.0 |
| 25 | 28.5 | 1.0 | 19.0 | 29.0 | 1.0 | 24.0 | 30.0 | 1.0 | 18.0 | 27.0 | 1.0 | 12.0 |
| 26 | 15.0 | 51.0 | 100.0 | 12.5 | 30.0 | 100.0 | 12.5 | 26.0 | 100.0 | 13.0 | 20.0 | 70.0 |
| 27 | 18.5 | 1.0 | 29.0 | 19.0 | 1.0 | 26.0 | 21.0 | 1.0 | 28.0 | 17.0 | 1.0 | 25.0 |
| 28 | 20.0 | 95.0 | 150.0 | 20.0 | 69.0 | 100.0 | 21.0 | 64.0 | 100.0 | 22.0 | 30.0 | 40.0 |
| 29 | 28.5 | 1.0 | 28.0 | 23.5 | 1.0 | 28.5 | 25.0 | 1.0 | 25.0 | 23.0 | 1.0 | 14.0 |
| 30 | 16.5 | 1.0 | 27.0 | 15.0 | 1.0 | 37.0 | 15.5 | 1.0 | 32.0 | 16.0 | 1.0 | 16.0 |
| CONTROL-1 | 17.0 | 1.0 | 20.0 | 19.0 | 1.0 | 21.0 | 18.5 | 1.0 | 19.0 | 16.5 | 1.0 | 18.0 |
| CONTROL-1 | 13.5 | 1.0 | 13.5 | 14.0 | 1.0 | 19.0 | 15.0 | 1.0 | 18.0 | 15.0 | 1.0 | 18.0 |

| | TIME (HOURS) | | | | | | | | | | | |
|---|---|---|---|---|---|---|---|---|---|---|---|---|
| | 4.0 | | | 8.0 | | | 16.0 | | | 24.0 | | |
| EX. | IMPEDANCE (OHMS) | TRBM (1)* (mm) | TRBM (3) (mm) | IMPEDANCE (OHMS) | TRBM (1) (mm) | TRBM (3) (mm) | IMPEDANCE (OHMS) | TRBM (1) (mm) | TRBM (3) (mm) | IMPEDANCE (OHMS) | TRBM (1) (mm) | TRBM (3) (mm) |
| 22 | 11.0 | 1.0 | 31.0 | 10.0 | 1.0 | 33.0 | 15.5 | 1.0 | 43.0 | 21.0 | 1.0 | 41.0 |
| 23 | 18.0 | 1.0 | 19.0 | 25.0 | 1.0 | 18.0 | 25.0 | 1.0 | 26.0 | 22.5 | 1.0 | 22.0 |
| 24 | 14.0 | 3.0 | 38.0 | 14.0 | 1.0 | 70.0 | 12.0 | 14.0 | 65.0 | 24.5 | 12.0 | 85.0 |
| 25 | 28.0 | 1.0 | 12.0 | 31.5 | 1.0 | 13.0 | 26.0 | 1.0 | 17.0 | 35.0 | 1.0 | 17.0 |
| 26 | 13.0 | 16.0 | 67.0 | 13.0 | 1.0 | 53.0 | 11.0 | 3.0 | 43.0 | 25.0 | 6.0 | 56.0 |
| 27 | 18.0 | 1.0 | 24.0 | 20.0 | 1.0 | 16.0 | 23.0 | 1.0 | 21.0 | 20.5 | 1.0 | 28.0 |
| 28 | 23.0 | 19.0 | 72.0 | 20.0 | 18.0 | 63.0 | 15.0 | 14.0 | 59.0 | 27.5 | 1.0 | 70.0 |
| 29 | 27.0 | 1.0 | 17.0 | 28.0 | 1.0 | 14.5 | 26.0 | 1.0 | 20.0 | 29.0 | 1.0 | 16.0 |
| 30 | 14.0 | 1.0 | 16.0 | 16.5 | 1.0 | 14.0 | 17.0 | 1.0 | 16.0 | 19.0 | 1.0 | 16.0 |
| CONTROL-1 | 17.0 | 1.0 | 16.0 | 15.5 | 1.0 | 14.0 | 110.0 | 1.0 | 19.0 | 4000.0 | 1.0 | 19.0 |
| CONTROL-1 | 15.0 | 1.0 | 17.0 | 15.0 | 1.0 | 18.0 | 12.0 | 11.0 | 25.0 | 2400.0 | 100.0 | 100.0 |

*TRBM (1) is Tack Rolling Ball Method as per PSTC (Pressure Sensitive Tape Council) Test Method #6 using a 11.1 mm in diameter 5.6 stainless steel ball.

Production of Patches

In another aspect of the invention, the hydrogels can be formulated to include pharmacologically active agents. The gels can then be constructed into PATCHES in the same manner as the electrodes described above.

In the manufacture of the PATCHES, pharmacologically active agents such as drugs may be added to the gel when the formulation is prepared and prior to irradiating. Alternatively, the pharmacologically active agent may be incorporated into a hydrogel, which has been crosslinked, by contacting the crosslinked gel with a solution or dispersion of the drug. In a further alternative, the drug can be incorporated into the hydrogel by either of the previously mentioned routes followed by ers such as salicylic acid, and the like; non-steroidal anti-inflammatory drugs such as piroxicam, ketoprofen, and the like; wound healing enhancers such as ketanserin, and the like; antihistamines such as terfenadine, and the like; anxiety/stress controllers such as diazepam, and the like; migraine headache preparations such as chlorpromazine, dihydroergotamine. Other pharmacologically active agents which may be employed include but are not limited to cisapride, motilim, risperadone, nicotine, povidone/iodine.

Indeed, large macromolecules such as proteins may also be incorporated into the gels of the present invention. See, for example, Gombotz, W. et al., in *Proceed. Intern. Symp.. Control. Rel. Bioact. Mater.*, (1992)

19:108–109, the disclosure of which is incorporated by reference herein. In particular, Gombotz et al. describe the incorporation of the protein, TGF-beta, into various hydrophilic gel formulations by exposing the different gel formulations to aqueous solutions of the protein.

Accordingly, and as shown in examples 31–38, compositions which incorporate various pharmacologically active agents can be incorporated into the hydrogel formulations. The formulations are cast into sheets of hydrogel and evaluated for drying characteristics.

Hydrogels Containing Additional Humectants and Buffers

Compositions which contain pharmacologically active agents such as those of examples 31–38 also may include a buffer system for stabilizing the pH of the gel when exposed to a specific environment. Suitable buffer systems may include phosphate buffer systems for providing a pH of 7, or carbonate buffer systems for stabilizing the gel in an acidic environment. These buffer systems are well known in the art. The specific amount of buffer system employed in these formulations can be readily determined by those skilled in the art.

Examples 31

To a solution of 82 g of deionized water, 4.0 g of ethylene glycol diamethacrylate as crosslinker, 0.4 g Liposorb ™ L-20 (Polysorbate ™ 20) from Lipo Chemicals Inc. (a surfactant to emulsify the crosslinker), 5.0 g of humectant-pentavitin ™ from Centerchem Inc., 0.031 g 40:1 aloe concentrate from Florida Food Products, 0.26 g Nipasept ™, Na salt preservative (a mixture of 70% methyl, 15% ethyl and 10% propylparaben salts) from Nipa Laboratories Inc., and 0.5 g phenoxyethanol is added and dispersed at approximately 100 RPM. 7.5 g of Polyox ™ WRS-205 poly(ethylene oxide) from Union Carbide Corporation is added slowly with rapid stirring at 300 RPM. When the polymer appears to be completely dispersed, agitation is slowed to approximately 25 RPM and continued for 16 hours. The hydrogel has a Brookfield relative viscosity of approximately 20,000 cP at a shear rate of 1.0/second.

Examples 32–38

The procedure of Example 31 is followed except that the components listed in Table XIV are employed to produce hydrogels.

Feedmixes of the components given in Table XIV are spread with a doctor blade into 50–60 mil thick sheets of hydrogels onto a thin plastic liner, and a top liner is placed on top of the cast layer of hydrogel. The top liners range in thickness from 1–7 mils, and are usually composed of low density polyethylene. A sheet of scrim is placed in the middle of the hydrogel to give it additional structural rigidity. The scrim may be a thick piece of non-woven fabric about 5–10 mil thick. Fabrics useful for manufacture of scrims include Delnet ™ X-230 from Hercules Inc., or Reemay ™ 2250 from Reemay, Inc.

TABLE XIV

| FEEDMIX COMPONENTS - GRAMS | EXAMPLE 31 | EXAMPLE 32 | EXAMPLE 33 | EXAMPLE 34 | EXAMPLE 35 | EXAMPLE 36 | EXAMPLE 37 | EXAMPLE 38 |
|---|---|---|---|---|---|---|---|---|
| Plasdone PVP K-90 | | | 20 | | 20 | | 20 | |
| Polyox WSR N-205 | 7.5 | 9.0 | | 9.0 | | 9.0 | | 9.0 |
| Nipasept, Na | 0.26 | 0.26 | 0.34 | 0.26 | 0.34 | 0.26 | 0.34 | 0.26 |
| KCl | | 5.0 | | 5.0 | | | | |
| Ethylene glycol dimethacrylate | 4.0 | | | | | | | |
| Methylene-bis-acrylamide | | 1.0 | | | | 1.0 | | 1.0 |
| Pentavitin | 5.0 | 20.0 | 7.5 | | | | | |
| Surfactol 365[1] | | | | 10.0 | 5.0 | 10.0 | 7.5 | 5.0 |
| Carbopol 934 NF[2] | | | 0.2 | | 0.2 | | 0.2 | |
| Liposorb L-20 | 0.4 | | | | | | | |
| Phenoxyethanol | 0.5 | 0.5 | | | | 0.5 | | 0.5 |
| Tween 80[3] | | | | | | | 0.37 | 0.37 |
| Span 80[4] | | | | | | | 0.37 | 0.37 |
| Na2HPO4 | | | 0.21 | | 0.21 | | 0.21 | |
| Na2H2PO4 | | | 0.09 | | 0.09 | | 0.09 | |
| Silver sulfadiazine | | | 1.0 | | 1.0 | | 1.0 | |
| Aloe (40:1 conc.) | 0.03 | | | | | 0.03 | | 0.03 |
| Deionized Water | 82 | 82 | 82 | 82 | 82 | 82 | 82 | 82 |

[1]Available from Caschem Corp., Bayonne, N.J.
[2]Available from B. F. Good Rich Co.
[3]Available from ICI Specialties, a division of ICI
[4]Available from ICI Specialties, a division of ICI Generally, the radiation dosage absorbed by the feed mixture is such that the material is cross-linked sufficiently to provide a gel but does not deleteriously affect the pharmacological agent. Accordingly, the hydrogel sheets provided in Examples 31–38 are irradiated with a Van der Graaf electron accelerator at 1.5 Mrad to produce a moderate tack crosslinked hydrogel. Irradiation is performed by setting the beam current to 0.95 mA with a conveyor line speed of 3.5 m/min.

The adhesivities of the hydrogels of Examples 30–38 are quantified using the Tack Roller Ball Method #6, (approved by the Pressure Sensitive Tape Council) using ball #3. The results are shown in Table XV.

TABLE XV

| Example No. | Dose (Mrad) | TRBM VALUE (mm)* |
|---|---|---|
| 31 | 1.5 | #3/46 |
| 32 | 1.5 | #3/7 |
| 33 | 1.5 | #3/17 |
| 34 | 1.5 | #3/19 |
| 35 | 0.5 | #3/25 |
| 36 | 1.1 | #3/15 |
| 37 | 5.0 | #1/15 |
| 38 | 1.5 | #3/12 |

*Either tack ball #1 or #3 is used

Drying Characteristics

Examples 39-44

Compositions of examples 39-44 are formulated as in examples 32-38 except that the components given in Table XVI are employed. Examples 39-40 serve as control examples that do not have humectant.

TABLE XVI

| Ingredients | Ex. 39 | Ex. 40 | Ex. 41 | Ex. 42 | Ex. 43 | Ex. 44 |
|---|---|---|---|---|---|---|
| Plasdone ™ PVP K90 | | 20 | | | 20 | 20 |
| Polyox ™ WSR N-301 | 4.0 | | | | | |
| Polyox ™ WSR N-205 | | | 7.5 | 7.5 | | |
| Nipasept ™, Na | | 0.19 | 0.26 | 0.26 | 0.26 | 0.34 |
| Ethylene glycol dimethacrylate | | 1.0 | | | 1.0 | |
| Methylene-bis-acrylamide | | | 1.0 | 1.0 | | |
| Surfactol ™ 365 | | | 15 | 10 | | 5.0 |
| Carbopol 934 NF | | 0.2 | | | 0.2 | 0.2 |
| Liposorb ™ L-20 | | 0.1 | | | 0.1 | |
| Phenoxyethanol | | 0.5 | 0.5 | 0.5 | | |
| Na$_2$HPO$_4$ | | | | | | 0.21 |
| NAH$_2$PO$_4$ | | | | | | 0.09 |
| Castor Oil[1] | | | | | 20 | |
| Crystal O ™ Aloe (40:1 conc.) | | | 0.031 | 0.031 | | |
| Deionized Water | 96 | 78.5 | 75.7 | 80.7 | 58.4 | 74.2 |

[1]From CasChem Co.

Comparison of the drying characteristics of the hydrogels of invention examples 41-44 which contain humectants with hydrogels of control examples 39-40 which do not contain humectants are compared. In this comparison, the bottom liners on which the hydrogels are formed are removed, and the hydrogels are placed under ambient conditions onto glass plates with the sticky side of the hydrogel facing down. The weight loss after three days of exposure is given in Table XVII. The tests were performed at 40% relative humidity and room temperature.

TABLE XVII

| Composition | Wt. loss |
|---|---|
| Example 39: 4% Polyox WSR-301 with no humectant | 58.5 |
| Example 40: 20% Plasdone PVP K-90 with no humectant | 46.4 |
| Example 41: 7.5% Polyox WSR-205 with 15% Surfactol 365 | 30.0 |
| Example 42: 7.5% Polyox WSR-205 with 10% Surfactol 365 | 34.0 |
| Example 43: 20% PVP K-90 with 20% castor oil | 25.0 |
| Example 44: 20% PVP K-90 with 5% Surfactol 365 | 32.0 |

Other embodiments of the invention will be apparent to those skilled in the art from consideration of the specification, or from practice of the invention disclosed herein. It is intended that the specification and examples be considered as exemplary only, with the scope and spirit of the invention being indicated by the following claims.

What is claimed is:

1. A non-stringy adhesive hydrophilic gel comprising an aqueous mixture of at least one crosslinkable water-soluble polymer, at least one humectant in an amount of from 1 to 40 weight percent, said amount being effective to extend the moisture retaining characteristics of said gel and to inhibit the ability of radiant energy to crosslink said polymer, and a crosslinking promoter in an amount effective to counteract said crosslink-inhibiting effect of said humectant, said aqueous mixture exposed to a dose of radiant energy effective to provide a non-stringy adhesive cohesive homogeneous hydrophilic gel that (i) retains moisture for longer periods than a hydrophilic gel prepared without said humectant; and (ii) remains flexible after being stored at about 0° F. for at least about 16 hours.

2. The gel of claim 1 which provides a rolling ball distance of at least about 10 mm using a 16.5 mm, 21.7 g stainless steel ball in a tack rolling ball method test.

3. The gel of claims 1 or 2 which further comprises a water-soluble electrolyte in an amount effective to reduce the transverse electrical resistance of the gel to an impedance at 60 Hz of less than about 1000 ohms.

4. The gel of claim 3 wherein the water-soluble electrolyte is present in an amount effective to reduce the impedance of the gel to less than about 100 ohms.

5. The gel of claims 1 or 2 in which said water-soluble polymer is poly(ethylene oxide), poly(vinyl pyrrolidone or mixtures thereof.

6. The gel of claim 1 wherein said water-soluble polymer is poly(vinyl pyrrolidone) and which further comprises poly(ethylene oxide) in an amount sufficient to increase the viscosity of the gel.

7. The gel of claims 1 or 2 which further comprises one or more additional uniformly dispersed additives selected from the group consisting of preservatives, stabilizers, fire retardants, pigments, refractive particles, bactericides, antibiotics, cosmetics, moisturizers, pharmacologic agents and mixtures thereof.

8. The gel of claim 7 in which each additive which is included is present at a concentration of about 0.001 to about 3 weight percent.

9. The gel of claims 1 or 2 which further comprises a scrim in intimate contact therewith.

10. The gel of claim 9 wherein the scrim comprises a low area-weight synthetic water-insoluble polymer.

11. The gel of claims 1 or 2 in which the humectant is castor oil, ethoxylated castor oil, saccharide isomerates, glycerol, propylene glycol, poly(ethylene glycol), N-methyl pyrrolidone, N-ethyl pyrrolidone, diacetone alcohol, γ-butyryl lactone, ethyl lactate and combinations thereof.

12. The gel of claims 1 or 2 in which the humectant is present at a concentration of about 1 to about 40 weight percent.

13. The gel of claim 3 in which the water-soluble electrolyte is an inorganic or organic salt.

14. The gel of claim 3 in which the water-soluble electrolyte is selected from the group consisting of potassium salts, sodium salts, magnesium salts, calcium salts and mixtures thereof.

15. The gel of claims 1 or 2 in which the aqueous mixture is exposed to a dose of radiant energy of at least about 0.5 Mrad to less than about 4 Mrad.

16. The gel of claim 15 in which the dose of radiant energy is less than about 2 Mrad.

17. The gel of claim 5 in which the water-soluble polymer is poly(vinyl pyrrolidone) and is present at a concentration of about 10 to about 30 weight percent.

18. The gel of claim 5 in which the water-soluble polymer is poly(ethylene oxide) and is present at a concentration of about 0.1 to about 20 weight percent.

19. The gel of claim 3 in which the amount of water-soluble electrolyte ranges from about 5 to about 8 percent by weight of said aqueous mixture.

20. The gel of claims 1 or 2 in which the crosslinking promoter is selected from the group consisting of N,N'- methylene-bis-acrylamide, ethylene glycol dimethacrylate, triethylene glycol dimethacrylate or mixtures thereof.

21. The gel of claim 20 in which said crosslinking promoter is present at a concentration of about 0.5 to about 3 weight percent.

22. The gel of claim 3 in which the water-soluble electrolyte is present at a concentration of about 0.1 to about 10 weight percent.

23. A method of forming a non-stringy adhesive hydrophilic gel which comprises:
preparing an aqueous mixture by adding at least one crosslinkable water-soluble polymer to water in an amount effective to provide a crosslinkable hydrophilic gel;
adding at least one humectant in an amount of from 1 to 40 weight percent, said amount being effective to extend the moisture retaining characteristics of the gel and to inhibit the ability of radiant energy to crosslink said polymer; and
adding a crosslinking promoter in an amount effective to counteract the crosslink inhibiting effect of the humectant; and
exposing said aqueous mixture to a dose of radiant energy effective to provide a non-stringy adhesive cohesive homogeneous hydrophilic gel that (i) retains moisture for longer periods than a hydrogel prepared without said humectant and (ii) remains flexible after being stored at about 0° F. for at least about 16 hours.

24. The method of claim 23 in which the resulting gel provides a rolling ball distance of at least about 10 mm using a 16.5 mm, 21.7 g stainless steel ball in a tack rolling ball method test.

25. The method of claims 23 or 24 which further comprises casting the aqueous mixture onto a substrate in a desired shape and configuration before exposing the cast mixture to radiant energy.

26. The method of claim 25 wherein the substrate remains in contact with the gel to form an article of manufacture.

27. A gel produced by the method of claims 23 or 24.

28. An article of manufacture produced by the method of claim 26.

29. An article of manufacture for therapeutic treatment of a wound comprising the gel of claims 1 or 2 in combination with a gel-supporting substrate.

30. The article of claim 29 wherein said gel has first and second sides, said substrate being in contact with said first side and further comprising a backing member that is in contact with said second side.

31. The article of claim 30 which further comprises score lines for defining a plurality of subunits of said article.

32. The article of claim 29 which is suitable for use as a wound dressing.

33. An article for therapeutic treatment of a wound comprising the gel of claim 3 in combination with a conductive gel-supporting substrate.

34. The article of claim 33 which is suitable for use as an electrode.

35. A method of electrical wound healing which comprises (i) contacting an area of the body affected by a wound with the electrode of claim 34 and (ii) applying an electrical impulse to said area through said electrode for a period of time effective to promote healing.

36. The method of claim 35 in which said electrode has an impedance of a sufficiently low value to minimize the occurrence of burns on the skin.

37. A hydrogel composition having adhesive and cohesive properties which is capable of transferring active agents contained in said hydrogel to a patient when said hydrogel composition is affixed to said patient, comprising:
an aqueous mixture in at least one crosslinkable water soluble polymer in an amount effective to provide a crosslinkable hydrophilic gel;
at least one humectant in an amount of from about 1 to 40 weight percent, said amount being effective to extend moisture retaining characteristics of the gel and to inhibit radiant energy from crosslinking said water soluble polymer;
a crosslinking promoter in an amount effective to counteract crosslinking inhibitory effects of said humectant; and
at least one active agent.

38. The hydrogel composition of claim 37 wherein said gel (i) retains moisture for longer periods than a hydrophilic gel prepared without said humectant; and (ii) remains flexible after being stored at about 0° F. for at least about 16 hours.

39. The hydrogel composition of claim 38 wherein said gel is non-stringy.

40. The hydrogel composition of claim 37 wherein said agent is selected from the group of topical analgesics, topical-counter irritants, antiseptics, appetite suppressants, asthma release preparations, decongestants, corn, wart and callous removers, non-steroidal anti-inflammatory drugs, wound healing enhancers, antihistamines, anxiety controllers, nicotine, and headache preparations.

41. The composition of claim 37 wherein said humectant is selected from the group of castor oil, ethoxylated castor oil, saccharide isomerates, glycerol, propylene glycol, poly(ethylene glycol), N-methylpyrrolidone, N-ethylpyrrolidone, diacetone alcohol, gamma-butyryl lactone, ethyl lactate and combinations thereof.

42. The composition of claim 37 wherein said crosslinkable water-soluble polymer is selected from the group of poly(ethylene oxide), poly(vinyl pyrrolidone) or mixtures thereof.

43. The composition of claim 37 wherein said crosslinking promoter is selected from the group consisting of N,N'-methylene-bis-acrylamide, ethylene glycol dimethacrylate, triethylene glycol dimethacrylate or mixtures thereof.

44. The composition of claim 37 wherein said agent is pharmacologically active.

45. The composition of claim 44 wherein said agent is a non-steroidal anti-inflammatory drug.

46. The composition of claim 45 wherein said agent is 5–50% of said gel composition.

47. A method of providing a hydrogel composition containing at least one active agent comprising:
providing an aqueous mixture of at least one crosslinkable water-soluble polymer in an amount effective to provide a crosslinkable hydrophilic gel;
adding at least one humectant in an amount of from 1 to 40 weight percent, said amount being sufficient to extend moisture retaining characteristics of said gel and to inhibit radiant energy from crosslinking said polymer;

adding a crosslinking promoter in an amount effective to counteract crosslinking inhibiting effects of said humectant; and exposing said mixture to radiant energy effective to provide a homogenous hydrophilic gel containing said active agent.

48. The method of claim 47 wherein said gel (i) retains moisture for longer periods than a hydrophilic gel prepared without said humectant;

and (ii) remains flexible after being stored at about 0° F. for at least about 16 hours.

49. The method of claim 48 wherein said gel is non-stringy.

50. The method of claim 47 wherein said active agent is incorporated into said mixture prior to exposing said mixture to radiant energy.

51. The method of claim 47 wherein said active agent is incorporated into said gel after exposing of said mixture to radiant energy.

52. The method of claim 47 wherein said agent is selected from the group of topical analgesics, topical-counter irritants, antiseptics, appetite suppressants, asthma release preparations, nicotine, decongestants, corn, wart and callous removers, non-steroidal anti-inflammatory drugs, wound healing enhancers, antihistamines, anxiety controllers, and headache preparations.

53. The method of claim 51 wherein said humectant is selected from the group of castor oil, ethoxylated castor oil, saccharide isomerates, glycerol, propylene glycol, poly(ethylene glycol), N-methylpyrrolidone, N-ethylpyrrolidone, diacetone alcohol, gamma-butyryl lactone, ethyl lactate and combinations thereof.

54. The method of claim 52 wherein said crosslinkable water-soluble polymer is selected from the group poly(ethylene oxide), poly(vinyl pyrrolidone) or mixtures thereof.

55. The method of claim 53 wherein said crosslinking promoter is selected from the group of N,N'-methylene-bis-acrylamide, ethylene glycol dimethacrylate, triethylene glycol dimethacrylate or mixtures thereof.

56. The method of claim 53 wherein said crosslinking promoter is 0.5-3% of said mixture.

57. The method of claim 47 wherein said agent is pharmacologically active agent.

58. The method of claim 57 wherein said pharmacologically active agent is a non-steroidal anti-inflammatory drug.

59. The method of claim 47 wherein said radiant energy is provided in the form an electron beam.

60. The method of claim 58 wherein said mixture is exposed to an electron beam to a dose of up to about 4 Mrad.

61. The method of claim 47 further comprising adhering a plastic liner to at least one side said gel.

62. The method of claim 23 in which the humectant is castor oil, ethoxylated castor oil, saccharide isomerates, glycerol, propylene glycol, poly(ethylene glycol), N-methyl pyrrolidone, N-ethyl pyrrolidone, diacetone alcohol, γ-butyryl lactone, ethyl lactate and combinations thereof.

63. A method of electrical wound healing which comprises (i) contacting an area of the body affected by a wound with an electrode comprising a non-stringy adhesive hydrophilic gel and a water-soluble electrolyte in an amount effective to reduce the transverse electrical resistance of the gel to an impedance at 60 Hz of less than about 1000 ohms, in combination with a conductive gel-supporting substrate, said gel comprising an aqueous mixture of at least one crosslinkable water-soluble polymer, at least one humectant in an amount of from 1 to 40 weight percent, said amount being effective to extend the moisture retaining characteristics of said gel and to inhibit the ability of radiant energy to crosslink said polymer, and a crosslinking promoter in an amount effective to counteract said crosslink-inhibiting effect of said humectant, said aqueous mixture exposed to a dose of radiant energy effective to promote a non-stringy adhesive cohesive homogeneous hydrophilic gel that (a) retains moisture for longer periods than a hydrophilic gel prepared without said humectant; and (b) remains flexible after being stored at about 0° F. for at least about 16 hours; and (ii) applying an electrical impulse to said area through said electrode for a period of time effective to promote healing.

64. The method of claim 63 in which said electrode has an impedance of a sufficiently low value to minimize the occurrence of burns on the skin.

65. The method of claim 63 in which the gel is formulated to provide a rolling ball distance of at least about 10 mm using a 16.5 mm, 21.7 g stainless steel ball in a tack rolling ball method test.

66. The method of claims 35 or 63 in which the water-soluble electrolyte is present in an amount effective to reduce the impedance of the gel to less than about 100 ohms.

* * * * *